(12) United States Patent
Muller et al.

(10) Patent No.: US 10,184,868 B2
(45) Date of Patent: Jan. 22, 2019

(54) DEVICE AND METHOD FOR TESTING TABLETS

(71) Applicant: ERWEKA GmbH, Heusenstamm (DE)

(72) Inventors: Werner G. Muller, Heusenstamm (DE); Levent Bozkurt, Heusenstamm (DE)

(73) Assignee: ERWEK GmbH, Heusenstamm (DE)

( * ) Notice: Subject to any disclaimer, the term of this patent is extended or adjusted under 35 U.S.C. 154(b) by 85 days.

(21) Appl. No.: 15/036,936

(22) PCT Filed: Aug. 15, 2014

(86) PCT No.: PCT/EP2014/067506
§ 371 (c)(1),
(2) Date: May 16, 2016

(87) PCT Pub. No.: WO2015/078600
PCT Pub. Date: Jun. 4, 2015

(65) Prior Publication Data
US 2016/0274013 A1    Sep. 22, 2016

(30) Foreign Application Priority Data

Nov. 27, 2013  (DE) .......................... 10 2013 113 126

(51) Int. Cl.
*G01N 3/40* (2006.01)
*G01N 33/15* (2006.01)

(52) U.S. Cl.
CPC .............. *G01N 3/40* (2013.01); *G01N 33/15* (2013.01); *G01N 2203/0087* (2013.01)

(58) Field of Classification Search
None
See application file for complete search history.

(56) References Cited

U.S. PATENT DOCUMENTS

| 4,236,413 | A | * | 12/1980 | Schmid | .................... G01N 3/08 73/821 |
| 4,884,663 | A | | 12/1989 | Kay | |
| 5,971,038 | A | * | 10/1999 | Fiedler | .................... G01G 17/00 141/173 |
| 6,260,419 | B1 | * | 7/2001 | Kramer | .................... G01N 3/40 73/78 |

(Continued)

FOREIGN PATENT DOCUMENTS

| DE | 298 24 199 U1 | 10/2000 |
| DE | 20 2008 010 27 | 11/2008 |

(Continued)

*Primary Examiner* — Jill E Culler
(74) *Attorney, Agent, or Firm* — Bond Schoeneck & King, PLLC; George McGuire

(57) ABSTRACT

The invention relates to a device and a method for testing tablets. In the process, a tablet is brought onto a rotary disk (1) by a transport rack (6). The rotary disk (1) positions the tablet (7) along one or more positioning surfaces by rotating. The positioning surfaces are preferably an abutment (2) and a stop (3). As soon as the tablet (7) is aligned on a positioning surface, a test of the tablet (7) is carried out by means of a breaking jaw (4). The breaking jaw can test the diameter as well as the breaking resistance of the tablet (7). The transport rack removes the tablet or the tablet debris from the rotary disk (1) after the tablet (7) has been checked.

14 Claims, 2 Drawing Sheets

(56) References Cited

U.S. PATENT DOCUMENTS

| | | | |
|---|---|---|---|
| 7,364,103 B2* | 4/2008 | Kraemer | G01N 3/04 |
| | | | 198/752.1 |
| 2005/0103132 A1 | 5/2005 | Bracher | |
| 2015/0040678 A1* | 2/2015 | Boss | G01N 3/40 |
| | | | 73/800 |

FOREIGN PATENT DOCUMENTS

| | | |
|---|---|---|
| EP | 2587261 A1 | 5/2013 |
| WO | WO 8907083 A1 | 8/1989 |
| WO | WO 2011/035818 A1 | 3/2011 |
| WO | WO 2013/061223 A2 | 5/2013 |
| WO | WO 2013083308 A1 | 6/2013 |

* cited by examiner

DEVICE AND METHOD FOR TESTING TABLETS

CROSS REFERENCE TO PRIOR APPLICATIONS

This is a U.S. National Phase application under 35 U.S.C. § 371 of International Patent Application No. PCT/EP2014/067506, filed Aug. 15, 2014, and claims the priority of German Patent Application No. 10 2013 113 126.3, filed Nov. 27, 2013, both of which are incorporated by reference herein in their entirety. The International Application is published in German on Jun. 4, 2015 as WO 2015/078600 A1 under PCT Article 21(2).

BACKGROUND OF THE INVENTION

The subject matter of the present invention is a device and a method for testing tablets. Within the context of quality control of tablets it is necessary to test tablets for properties such as length, width, breaking resistance and weight. The Deutsche Arzneibuch (German Pharmacopoeia) contains the relevant legal regulations. This process should, if possible, be carried out automatically, so that a large number of tablets can be tested within a short period of time. Moreover, it has to be ensured that tablets of different shapes and sizes can be correctly positioned in order to allow an error-free measurement to be carried out. The prior art includes a number of devices and methods that are suitable for this purpose.

German Patent Document DE 197 33 436 C2 describes a tablet testing device for testing oblong tablets. Here, the tablets to be tested are initially fed to weighing scales by a feeding device and are subsequently transferred to a transport device by the latter. On the transport device, the tablets are deposited in a predefined position, so that further tests can be carried out. The correct orientation of the tablets as they are deposited on the transport device is here achieved by means of the fact that the scales pan has a bottom in the form of a gutter. This ensures that the oblong tablets are correctly orientated. Moreover, a stumbling block, such as a wedge, may be located on the transport device, which is provided for cases where the tablet falls onto the transport device head first. In this case, the stumbling block ensures that the tablet tilts onto its long side. According to this invention, a correct orientation of a tablet is effected, however, the tablet is exposed to site considerable forces during its transfer through the gutter, which could cause them to be damaged.

German Patent Document DE 10 2006 004 215 B4 discloses a break resistance testing device for tablets of different shapes and sizes. In order to realise the orientation of the tablets, two centering rollers are used, which are driven in opposite directions and are arranged next to each other. If an oblong tablet is placed on the rollers, the rotation of the latter ensures that the oblong tablet orientates itself in the longitudinal direction between the rollers. Subsequently, the resistance may be tested by means of a breaking jaw. In order to ensure that tablets of different shapes and sizes can be orientated, the device is equipped with a pivotable positioner that can orientate the rollers differently. The orientation process is carried out quickly, however, due to the use of rollers it may be difficult to clean the apparatus after a break resistance test.

Utility Model DE 298 24 199 U1 discloses a system for carrying out hardness tests on specimens, which adopts an alternative approach. Here, the tablet is placed on a test table, but no orientation of the tablet is carried out after that. Instead, the orientation of the specimen is determined by means of a device for position detection. Subsequently, a pressure piston as well as a counter bearing, which are used for hardness testing of the tablet, are appropriately orientated so that the testing of the tablet can be carried out. However, this invention requires a complex and cost-intensive design that must comprise means for image detection.

PCT Publication WO 2013/061223 A2 discloses a method and a device for checking tablets, which orientates the tablets with the aid of a pivotable rocker. The tablet is here deposited on the initially horizontal rocker, which now carries out a pivoting movement. As a result of the effect of gravity and the pivoting movement it is achieved that the tablet orientates itself on a positioning surface. The positioning surface has here a concave shape that extends along the shape defined by the movement of the rocker. In order to support the correct orientation of the tablet, the pivotable rocker may additionally be inclined, at an angle to the positioning surface, or may have an additional device on the side that is opposite the positioning surface, which carries out a pre-orientation of the tablet. Once the rocker has been positioned and returned into a horizontal position, the tablet is tested. Since the positioning is here carried out under the effect of gravity and the rocking movement has to be carried out at a sufficient speed, the risk that the forces acting on the tablet during the orientation process might be too high cannot be eliminated here either.

DETAILED DESCRIPTION OF THE PREFERRED EMBODIMENT(S) AND INVENTION

Figure 1:
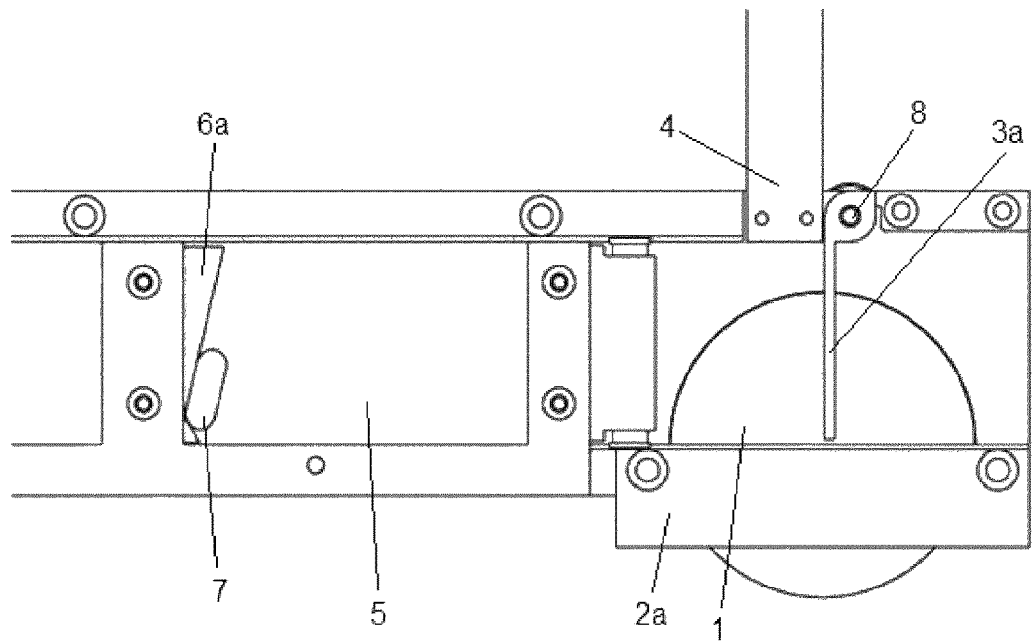
FIG. 1 is a schematic diagram according to an exemplary embodiment of the present invention.

It is therefore the object of the present invention to provide a device and a method for testing tablets, in which the tablet is orientated prior to being tested in a gentle and rapid manner that is easy to implement, whilst easy cleaning must be ensured at the same time.

This object is achieved by means of a device and a method according to claim 1. The device comprises a rotary disc (1) designed for positioning a tablet (7) for testing. At least one positioning surface (2a, 3a) is located above the rotary disc (1), along which the tablet (7) can be positioned as a result of the rotation of the rotary disc (1) in a direction of rotation.

A positioning surface (2a) is preferably implemented as an abutment (2). As a result of the rotation of the rotary disc (1), the tablet (7) is moved up to the abutment (2) and is positioned along the abutment (2).

The tablet is preferably an oblong tablet which, due to its shape, orientates itself lengthwise on the positioning surface (2a, 3a). However, it is also possible to position tablets of other shapes, for example round tablets. Here, the process merely leads to the tablet being moved up to the positioning surface (2a, 3a), so that a test can be carried out. With regard to the deliberations provided below it has to be noted that the testing process is carried out without any human intervention. Thus, for example, the rotary disc (1) is driven by a motor. Preferably, the device has a computer system that does not only control the movement processes but also stores the measured values.

According to one possible embodiment of the invention, a further positioning surface (3a) is provided, which is designed as a stop (3). The stop (3) may be disposed at any desired angle to the abutment (2), it will however preferably be disposed at a right angle to the abutment (2). An orientation of the tablet (7) on the stop (3) is carried out when the rotary disc (1) rotates in a direction of rotation that is opposite to the direction of rotation that leads to the tablet (7) being orientated on the abutment.

Preferably, the rotary disc (1) continues its rotational movement even after an orientation of the tablet (7) on the respective positioning surface (2a, 3a) has been carried out. It is here particularly advantageous if the rotational movement is continued during the testing of the tablet (7).

If it is not desired for the rotation of the rotary disc (1) to be continued during the orientation of the tablet (1) on the abutment or the stop, it is possible according to a further embodiment to suspend the rotation of the rotary disc (1) as soon as a successful orientation has been achieved. The suspension of the rotation may be carried out once a certain period of time has elapsed that is sufficient for a successful orientation of the tablet (7) to be achieved under usual circumstances. Alternatively, a sensor system may be used to check whether the orientation of the tablet (7) has been successful, and at this point the rotation of the rotary disc (1) may be suspended. A sensor system suitable for this purpose may for example be implemented by a camera system.

The abutment (2) and the stop (3) are implemented as flat surfaces which are positioned vertically above the rotary disc (1), with a distance as small as possible existing between the rotary disc (1) and the respective positioning surface 3a). The distance between the rotary disc (1) and the respective positioning surface (2a, 3a) must not be so great that a tablet (7) to be tested can get underneath the positioning surface (2a, 3a) and can therefore no longer come to lie on the positioning surface (2a, 3a) and can therefore not be orientated thereon by the rotation of the rotary disc (1).

The abutment (2) and the stop (3) should be orientated at a right angle relative to each other, however, they may also be orientated at any other angle relative to each other. The positioning surfaces (2a, 3a) are attached relative to the rotary disc (1) in such a way that the imaginary line that is defined by the respective positioning surface (2a, 3a) extends in each case as closely as possible to the centre of the rotary disc (1) or ideally through the centre thereof.

In order to allow a better positioning of the tablet along the positioning surfaces (2a, 3a), the positioning surfaces (2a, 3a) could have a specific shape. According to the invention, a flat shape is regarded as particularly advantageous. However, it is also possible to provide the positioning surfaces (2a, 3a) with a concave shape. Moreover, it is possible to provide the positioning surfaces (2a, 3a) with a roughened surface or with a special pattern, which allow an improved orientation of the tablets.

Similarly, the surface of the rotary disc (1) may have a particular characteristic in order to allow a better transport of the tablet (7). Thus, a slightly rough surface is to be regarded as advantageous.

In a further embodiment, weighing scales are integrated into the rotary disc (1) or below the rotary disc. These can be used to determine the weight of the tablet (7) deposited on the rotary disc (1).

It is further preferred if the device has a breaking jaw (4) that can be moved in the direction of the abutment (2). By means of the breaking jaw (4), the diameter of the tablet (7) can be measured, which is orientated along the at least one positioning surface (2a, 3a), wherein the diameter is measured in the direction of movement of the breaking jaw (4). If the tablet (7) is an oblong tablet, then the width of the tablet (7) is initially measured, and subsequently, in a second position, the length.

Preferably, the breaking jaw (4) is further suitable for carrying out a test of the hardness of a tablet (7) that is orientated along the at least one positioning surface (2a, 3a).

In a preferred embodiment of the device, a rake (6a) is provided that pushes the tablet material from the rotary disc (1) once the test has been carried out.

If the further positioning surface (3a) is designed as a stop (3), it is advantageous if the stop (3) is fixed to a rotary joint (8) with a spring that is provided for yielding to a movement by the rake (6a) and for returning into its original position by itself.

It is moreover preferred if the rake (6a) is a transport rake (6), by means of which the tablet (7) can be pushed onto the rotary disc (1) prior to the test. Thus, the transport rake (6) can both transport the tablet (7) onto the rotary disc (1) and push the tablet or tablet residues from the rotary disc (1) after completion of the test.

A further subject matter of the present invention is a method for testing tablets.

A preferred method for testing tablets includes at least the following steps. A tablet (7), preferably an oblong tablet, is deposited on the rotary disc (1). The tablet (7) comes, as a result of the rotation of the rotary disc (1), into contact with a positioning surface (2a, 3a) and is orientated thereon. The orientation of the tablet (7) is achieved as a result of the fact that the latter comes, as a result of the rotation of the rotary disc (1), into contact with a positioning surface (2a, 3a) and is orientated on this positioning surface (2a, 3a), as a result of the rotation of the rotary disc (1), along the longitudinal axis thereof. The rotation of the rotary disc (1) may be carried out even before the tablet (7) is deposited on the rotary disc (1), or it may not start until after the tablet (7) has been deposited on the rotary disc (1). Subsequently, at least one test of the tablet (7) is carried out.

Preferably, for testing the tablet (7) in a first position, the latter is positioned by rotating the rotary disc (1) in a first direction, so that the tablet (7) is orientated along a positioning surface which is preferably an abutment (2). In order to carry out a further test, the tablet (7) is positioned for testing in a further position by rotating the rotary disc (1) in a direction opposite to the direction of the previous rotation, so that the tablet (7) impinges on a positioning surface (3a), which is preferably a stop (3), and is orientated therealong. If the tablet m is an oblong tablet, then initially the width of the tablet (7) is measured in a first position, and subsequently the length is measured in a second position. Once the length has been measured, the breaking resistance is tested in the same position.

Preferably, the method according to the invention is carried out as follows:

1. A tablet (7), preferably an oblong tablet, is deposited on the rotary disc (1).

2. The tablet is orientated on a first positioning surface (2a) by means of the rotation of the rotary disc (1).

3. A test of the width of the tablet (7) is carried out.

4. The tablet is orientated on a further positioning surface (3a) by means of the rotation of the rotary disc (1), which is carried out in a rotary direction that is opposite to the rotary direction during the first positioning.

5. A test of the length of the tablet (7) is carried out.

6. A breaking test of the tablet (7) is carried out.

7. The residues of the tablet (7) are removed from the rotary disc (1).

Alternatively however, depending on the desired testing objectives, another process sequence is also possible, such as for example a variant, in which only one measurement of the diameters, but not a breaking test is carried out, or only a breaking test without a prior diameter measurement is carried out. The term diameter measurement comprises, in terms of the present invention, a measurement of the width and/or of the length of the tablet.

It will be described below in which way the diameter and the breaking resistance of the tablet (7) can be tested, how the tablet (7) can be deposited on the rotary disc (1) and which possibilities there are in order to remove the tablet (7) or the residues thereof from the rotary disc (1) after the test.

The testing of the tablet (7) is carried out by means of a breaking jaw (4). The breaking jaw (4) carries out a movement in the direction of the abutment (2). This is driven by a motor. The breaking jaw (4) is designed to test the diameter of the tablet (7) as well as the breaking resistance thereof. The test of the dimensions is here carried out by moving the breaking law (4) in the direction of the abutment (2) until a predefined counterforce occurs. This counterforce indicates that the breaking jaw (4) has impinged on the tablet (7).

The distance travelled by the breaking jaw (4) is stored, and from this the diameter of the tablet (7) can optionally be directly calculated. The diameter of the tablet (7) is calculated from the maximum distance that can be travelled between the initial position of the breaking jaw (4) and the abutment (2) minus the distance actually travelled by the breaking jaw.

The measurement of the diameter can be carried out either after the tablet (7) has been positioned along the abutment (2) or once the tablet (7) has been orientated along the stop (3). If a positioning along the abutment (2) was carried out, the width diameter is measured by the breaking jaw (4). If a positioning along the stop (3) was carried out, the length diameter of the tablet (7) is measured by the breaking jaw (4).

Preferably, the breaking jaw (4) is designed to carry out a measurement of the breaking resistance of the tablet (7). To this end, the breaking jaw (4) is moved in the direction of the abutment until a predefined counterforce occurs on the breaking jaw (4). This indicates that the breaking jaw (4) has reached the tablet (7). Subsequently, the force exerted by the breaking jaw (4) is increased until the tablet (7) breaks. The force exerted by the breaking jaw (4), which was necessary to effect a break of the tablet (7), is here stored in the integrated computing system of the device. A measurement of the breaking resistance can be carried out only if the tablet (7) was previously orientated on a positioning surface (2a, 3a). If the orientation was carried out on the abutment (2), then a test of the breaking resistance in relation to the long side of the tablet (7) is carried out. If the orientation was carried out on the stop (3), a test of the breaking hardness is carried out in relation to the short side of the tablet (7).

In a further embodiment, the tablet (7), or the residues thereof, are pushed from the rotary disc (1) by a rake (6a), once the test is completed. In an advantageous variant of the invention, the rake (6a) carries out a movement in the direction of the stop (3). This movement is supported by motor power. Here too, the control of the process is carried out by a computing unit integrated into the test device. According to this variant of the invention, the stop (3) is fixed to a rotary joint (8) with a spring or to a motorised rotary joint (8). In the case of a rotary joint (8) with a spring, the stop (3) yields to the movement of the rake (6a). Once the rake (6a) has pushed the tablet (7) or the residues thereof from the rotary disc (1), it returns into its starting position.

As a result of the spring force acting on the rotary joint (8), the stop (3) also returns into its starting position. In the case of a motorised rotary joint (8), the stop is moved by motor force, so that it will not come into contact with the rake (6a), when the latter pushes the residues of the tablet (1) from the rotary disc (1). If the rake (6a) moves into its starting position, then also the starting position of the stop (3) is restored by motor force. According to the invention, the tablet (7) or the residues thereof can also be removed from the rotary disc (1) in a different way, for example by means of pressurised air.

It is contemplated that the rotation of the rotary disc (1) is continued during the test or that the rotation of the rotary disc (1) is suspended as soon as successful orientation of the tablet (7) has been carried out.

Further, the rake may be designed as a transport rake (6) that is suitable for pushing the tablet (7) onto the rotary disc (1) via a transport rail (5). However, the transport of the tablet (7) onto the rotary disc can also be carried out in a different way, for example, the tablet (7) can be advanced to the rotary disc (1) by means of a transport gutter. Preferably, the transport rake (6) is moreover suitable for taking over the function of the rake described above, which is used for cleaning the rotary disc (1).

In a preferred embodiment of the method according to the invention, the positioning of the tablet (7) is carried out on at least one positioning surface (2a, 3a), which is flat or concave.

It is further preferred if the tablet (7) deposited on the rotary disc (1) is weighed by a weighing mechanism that is part of the rotary disc (1).

The device according to the invention and the method according to the invention will be explained in more detail below with reference to FIGS. 1 to 4.

FIG. 1 shows an embodiment of the device according to the invention. A particularly advantageous embodiment of the invention is described in FIGS. 2 to 4. A brief description of the figures follows below:

FIG. 1 shows a top view of a possible embodiment in a first method step, comprising a rotary disc (1), first positioning surface (2a), a further positioning surface (3a), a breaking jaw (4), a transport rail (5), a rake (6a) and a tablet (7), wherein the tablet (1) is located on the transport rail (5).

Figure 2:
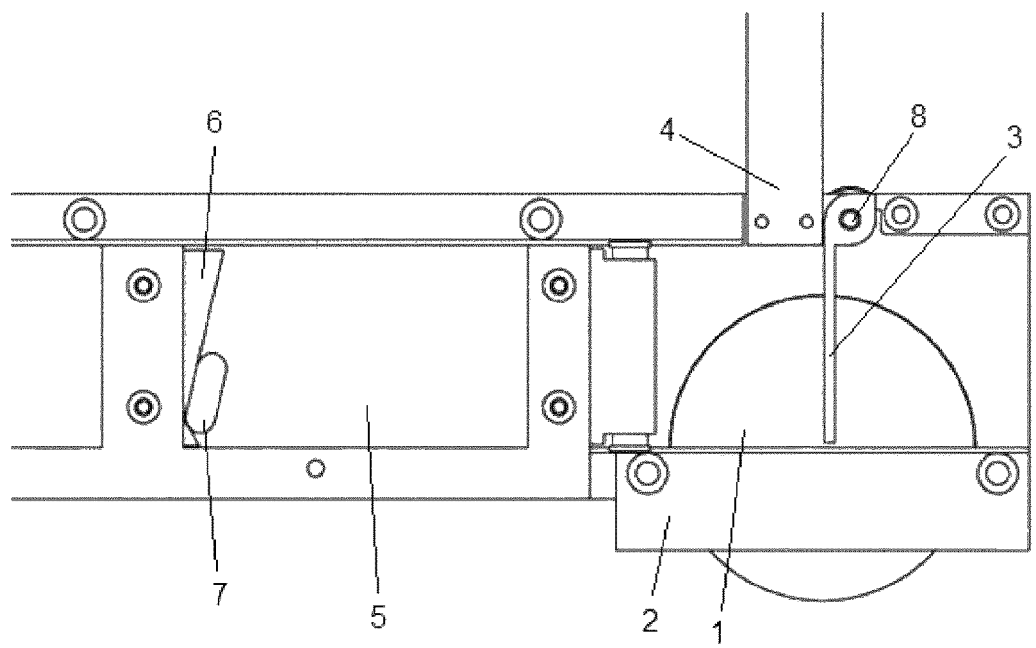
FIG. 2 is a schematic diagram according to an exemplary embodiment of the present invention.

FIG. 2 shows a top view of a preferred embodiment in a first method step, comprising a rotary disc (1), an abutment (2), a stop (3), a breaking jaw (4), a transport rail (5), a transport rake (6) and a tablet (7), wherein the tablet (7) is located on the transport rail (5).

Figure 3:
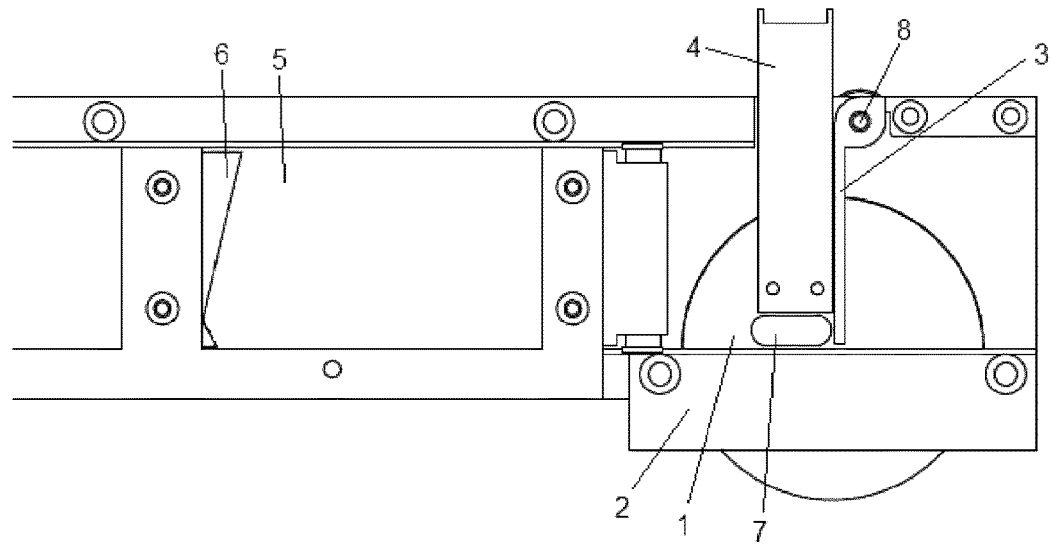
FIG. 3 is a schematic diagram according to an exemplary embodiment of the present invention.

FIG. 3 shows a top view of the same embodiment as in FIG. 1 in a subsequent method step, wherein the tablet (1) is orientated on the abutment (2).

Figure 4:
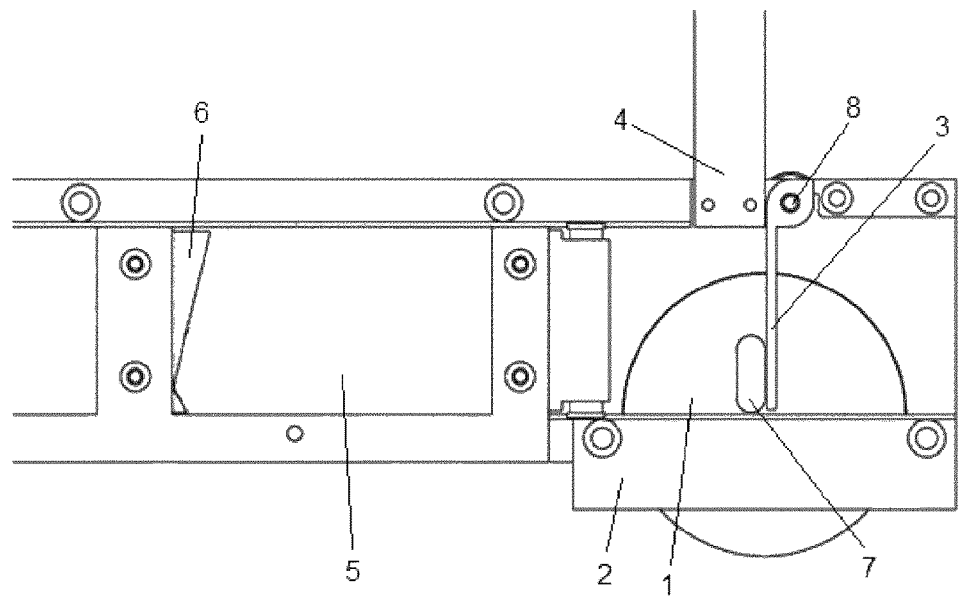
FIG. 4 is a schematic diagram according to an exemplary embodiment of the present invention.

FIG. 4 shows a top view of the same embodiment as in FIG. 2 and in FIG. 3 in a further method step, wherein the tablet (1) is orientated on the stop (3).

The device according to the invention preferably comprises a rotary disc (1), a first positioning surface (2a), a further positioning surface (3a), a breaking jaw (4), a transport rail (5), a rake (6a) and a tablet (7), wherein the tablet (1) is located, in this view, on the transport rail (5) (FIG. 1). If the rake (6a) is a transport rake (6), then the latter can transport the tablet (7) onto the rotary disc (1).

A tablet (7), preferably an oblong tablet, is deposited on the rotary disc (1). The tablet (7) comes into contact with a first positioning surface (2a), which is preferably an abutment (2), as a result of the rotation of the rotary disc (1) in a first direction, and is orientated thereon. The orientation of the tablet (7) is carried out as a result of the fact that the latter comes into contact with a positioning plane as a result of the rotation of the rotary disc and is orientated on this positioning plane as a result of the rotation of the rotary disc along the longitudinal axis thereof. The rotation of the rotary disc (1) can here be carried out as early as prior to the tablet being deposited on the rotary disc, or may not start until after the tablet is located on the rotary disc. Subsequently, at least one test of the tablet (7) is carried out. In order to carry out a further test, the tablet (7) is positioned for testing in a further position as a result of the fact that the rotary disc rotates in a direction opposite to the direction of the previous rotation, so that the tablet (7) is orientated along a positioning surface (3a), which is preferably a stop (3).

In a preferred embodiment of the device, a rake (6a) is provided which pushes the tablet material from the rotary disc (1) once the test is completed. If the rake (6a) is a transport rake (6), the latter can push the tablet (7) onto the rotary disc (1) prior to the test. Thus, the transport rake (6) can both transport the tablet onto the rotary disc (1) and push the tablet (7) or tablet residues from the rotary disc (1) once the test is complete.

A preferred method for testing tablets according to the present invention will be described below with reference to FIGS. 2 to 4. In the initial condition, the tablet (7) is located on a transport rail (5). The singling of the tablets has been carried out in a previous step, so that always only one tablet (7) at a time is located on the transport rail (5). The transport rake (6) will now carry out, supported by a motor, a movement in the direction of the rotary disc (1) and as a result pushes the tablet (7) onto the rotary disc (1). The transport rake (6) moves from the rotary disc (1) in the direction of its starting position, but only so far that it is no longer positioned over the rotary disc (1). As soon as the tablet (7) reaches the rotary disc (1), the rotary disc (1) starts a motor-supported rotation in the counter-clockwise direction. As a result, the tablet (7) is positioned along the abutment (2).

Whilst a rotary disc (1) continues to rotate in the counter-clockwise direction, the breaking jaw (4) is moved in the direction of the abutment (2) until a predefined counterforce occurs. The distance travelled is recorded by a computing unit that is integrated into the testing device and is also used for controlling the movements of the device. This method step is shown in FIG. 3. Due to the orientation of the tablet (7), its width is determined thereby.

Subsequently, the breaking jaw (4) moves back into its starting position and the rotary disc (1) starts to rotate in the clockwise direction. As a result, the tablet (7) is orientated on the stop (3). This method step is shown in FIG. 4. The rotary disc (1) continues its rotation, whilst the breaking jaw moves in the direction of the abutment (2). The movement of the breaking jaw (4) is suspended as soon as the predefined counterforce occurs on the breaking jaw (4). The distance travelled is recorded by the computing unit. Due to the orientation of the tablet (7), the length of the tablet (7) can be determined on the basis of the distance travelled. The breaking jaw (4) remains in its current position and now exerts a force in the direction of the abutment (2), which is linearly increased. As soon as the tablet (7) breaks, the force exerted at that point is recorded by the computing unit. The rotary disc (1) terminates its rotation and the breaking jaw (4) is moved back into its starting position.

Subsequently, the transport rake (6) moves in the direction of the stop and as a result pushes the residues of the tablet (7) from the rotary disc (1). In the course of this, the transport rake (6) impinges on the stop (3). Since it is fixed to a rotary joint (8), the stop (3) yields to the transport rake (6). The transport rake (6) now returns into its starting position. In the course of this, also the stop (3) resumes its starting position, which is brought about by a spring integrated in the rotary joint. A further tablet (7) can now be placed on the transport rail (5), so that the process can be restarted.

LIST OF REFERENCE NUMERALS

1 Rotary disc
2a Positioning surface
2 Abutment
3a Positioning surface
3 Stop
4 Breaking jaw
5 Transport rail
6a Rake
6 Transport rake
7 Tablet
8 Rotary joint

The invention claimed is:

1. A device for testing tablets, comprising a rotary disc (1) designed to position a tablet (7) for testing, characterised in that
a first positioning surface (2a) is designed above said rotary disc (1) as an abutment (2), along which the tablet (7) can be positioned by rotating the 5 rotary disc (1) in a first direction of rotation, and a second positioning surface (3a), which is adjacent to the first positioning surface (2a), is designed as a stop (3), along which the tablet (7) can be positioned by rotating the rotary disc (1), when the direction of rotation is opposite to the first direction of rotation, the abutment (2) and the stop (3) implemented as flat surfaces 10 which are positioned vertically above the rotary disc (1),
with a distance between the rotary disc (1) and the respective positioning surface (2a, 3a) small enough that a tablet (7) to be tested cannot move underneath the positioning surface (2a, 3a) and therefore be unable to lie on the positioning surface (2a, 3a) and be oriented thereon by the rotation of the rotary disc (1), and
a rake is provided that pushes the tablet material from the rotary disc (1) once the test is completed and that is a transport rake (6), by means of which the tablet (7) can be pushed onto the rotary disc (1) prior to the test.

2. The device as claimed in claim 1, characterised in that the abutment (2) and 20 the stop (3) are orientated at an angle of 90° relative to each other.

3. The device for testing tablets as claimed in claim 1, characterised in that the device is provided with a breaking jaw (4) that can be moved in the direction of the abutment (2), said breaking jaw (4) being suitable for measuring the diameter of the tablet that is orientated along the at least one positioning surface, wherein the 25 diameter is measured in the direction of the direction of movement of the breaking jaw (4).

4. The device as claimed in claim 3, characterised in that the breaking jaw (4) is suitable for carrying out a test of the breaking resistance of a tablet (7) that is orientated along the at least one positioning surface (2a, 3a).

5. The device as claimed in claim 1, characterised in that the stop (3) is fixed to a rotary joint (8) with a spring, which is intended to yield to a movement by the 5 rake and to return by itself into its original position.

6. The device as claimed in claim 1, characterised in that the at least one positioning surface (2a, 3a) is formed as a flat or a concave surface and/or a computing system is integrated into the testing device, which is intended for controlling processes and recording measured values.

7. A method for testing tablets, wherein a tablet (7) is deposited on a rotary disc (1), the tablet (7) is orientated, and subsequently at least one test is carried out on the tablet (7), characterised in that for testing the tablet (7) in a first position, the latter is positioned by rotating the rotary disc (1) in a first direction, so that the tablet (7) is orientated along a positioning surface (2a), which is an abutment (2), and for testing in a second position, the tablet (7) is positioned by rotating the rota-ry disc in a direction opposite to the first direction of rotation, so that the tablet (7) is orientated along a positioning surface (3a) that is adjacent to the first positioning surface (2a), which is a stop (3), and the test of the tablet (7) is carried out by a breaking jaw (4) that carries out a movement in the direction of the abutment (2), whilst the rotary disc (1) continues to rotate until a predefined counterforce occurs.

8. The method as claimed in claim 7, characterised in that the breaking jaw (4) carries out the test of the diameter of the tablet (7) that is orientated along the at least one positioning surface, by carrying out a movement in the direction of the abutment (2) until a counterforce according to a predefined value occurs on the breaking jaw (4).

9. The method as claimed in claim 7, characterised in that the breaking jaw (4) carries out a test of the breaking resistance of a tablet (7) that is orientated along the at least one positioning surface (2a, 3a), by carrying out a movement in the direction of the abutment (2) until a counterforce according to a predefined value occurs on the breaking jaw (4), whereupon the force exerted by the breaking jaw 5 (4) is increased in the direction of movement until the tablet (7) breaks.

10. The method as claimed in claim 7, characterised in that the rotation of the rotary disc is continued during the test or in that the rotation of the rotary disc is suspended as soon as a successful orientation of the tablet has been carried out.

11. The method as claimed in claim 7, characterised in that a rake pushes the tablet material from the rotary disc (1) once the test has been completed.

12. The method as claimed in claim 11, characterised in that the rake is guided in the direction of the stop (3) that is fixed to a rotary joint (8) with a spring, and in that the stop (3) is pushed away by the effect of the force of the rake and returns by itself into its starting position by the spring action when the rake is moved back into its starting position.

13. The method as claimed in claim 12, characterised in that the rake is a transport rake (6) that pushes the tablet (7) onto the rotary disc (1) prior to the test.

14. The method as claimed in claim 7, characterised in that the positioning is carried out on at least one positioning surface that is flat or concave and/or in that an integrated computer system controls processes and records measured values.

* * * * *